United States Patent [19]

Kanner

[11] Patent Number: 5,306,260
[45] Date of Patent: Apr. 26, 1994

[54] INDEXING CANNULA SUPPORT MECHANISM

[75] Inventor: Rowland W. Kanner, Guntersville, Ala.

[73] Assignee: Ryder International Corporation, Arab, Ala.

[21] Appl. No.: 969,025

[22] Filed: Oct. 30, 1992

[51] Int. Cl.⁵ .............................................. A61M 5/00
[52] U.S. Cl. .................................. 604/263; 128/754
[58] Field of Search ........................... 604/263, 274; 128/749–755, 762; 206/363–367, 443; 606/167, 170

[56] References Cited

U.S. PATENT DOCUMENTS

| | | | |
|---|---|---|---|
| 4,497,325 | 2/1985 | Wedel | 128/754 |
| 5,121,751 | 6/1992 | Panalletta | 128/754 |

*Primary Examiner*—C. Fred Rosenbaum
*Assistant Examiner*—V. Alexander
*Attorney, Agent, or Firm*—Trexler, Bushnell, Giangiorgi & Blackstone

[57] ABSTRACT

A tissue sampling instrument for use with various needle gauges to extract tissue samples includes a support structure, preferably rotatable, including a plurality of needle support seats having different seat dimensions corresponding to respective different needle circumferences. The seats are arranged on the support structure to enable selective access and positioning of each seat in order to selectively support the corresponding needle circumference thereon and ensure accurate linear longitudinal motion of the needle against the selected seat in the tissue sampling procedure. The preferred rotatable support structure can be mounted on an end wall of the body of the instrument so that the supported needle projects from the end wall.

7 Claims, 2 Drawing Sheets

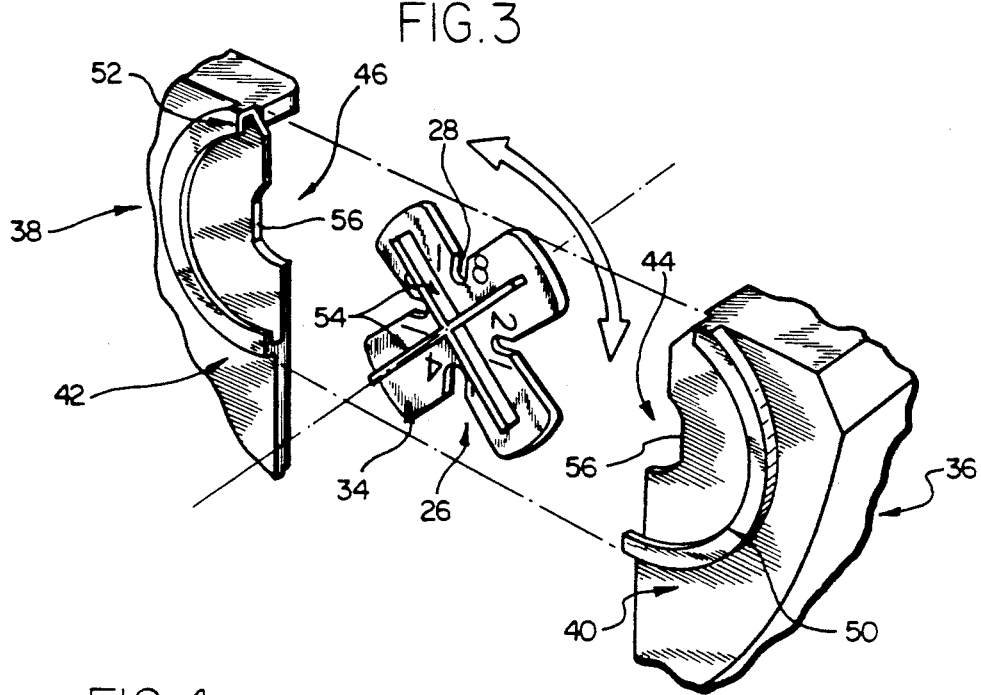
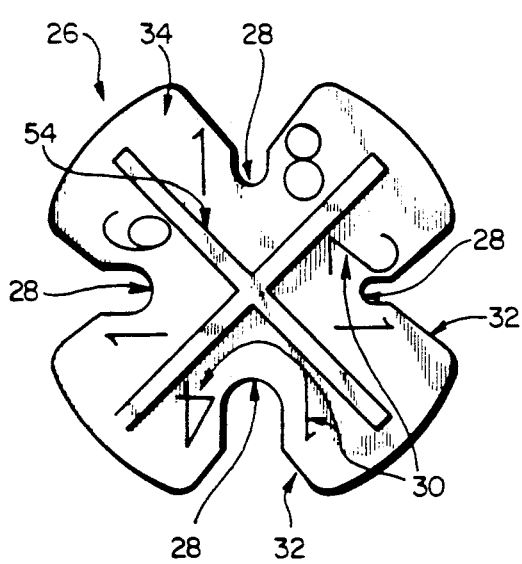
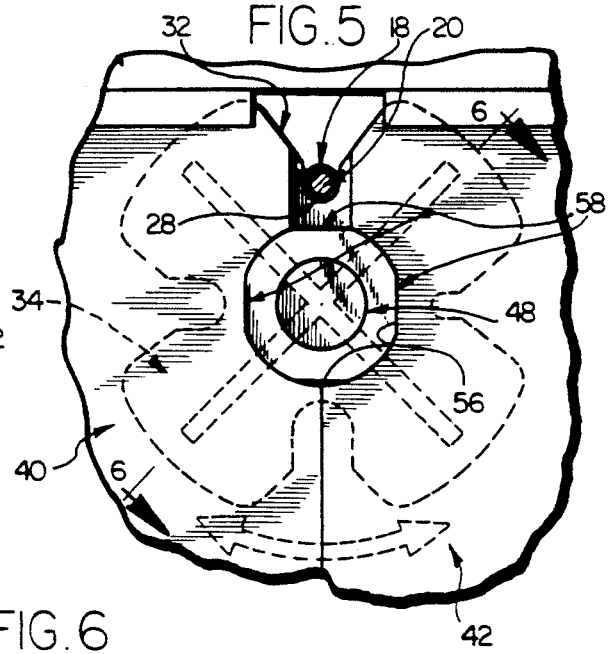
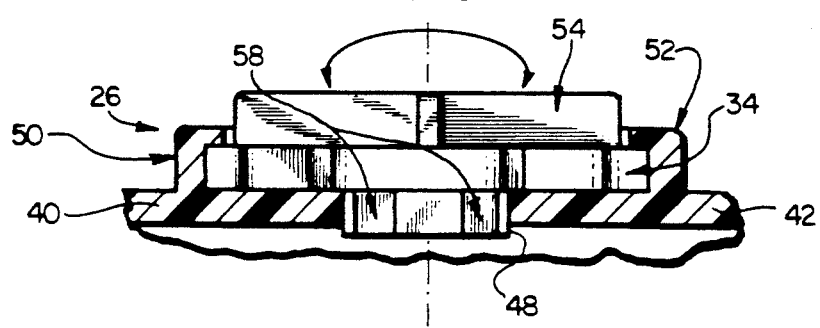

INDEXING CANNULA SUPPORT MECHANISM

BACKGROUND OF THE INVENTION

The present invention relates to needle instruments for obtaining tissue samples to be used for example in biopsy procedures. More particularly, the invention relates to improved instruments accommodating a variety of biopsy needle assemblies of differing gauges for sampling tissue.

In diagnostic tissue sampling, for example, of prostate tissue, needle assemblies have been developed which capture a longitudinal, or core sample of the tissue which is extracted for diagnosis. Conventionally, the needle assembly has a hollow outer cannula needle which cooperates with an inner stylet needle to cut and capture a core of the tissue within a notch formed in the inner stylet as described for example in U.S. Pat. No. 5,121,751, the text of which is incorporated by reference herein, and which illustrates an operating mechanism for a biopsy needle assembly. Typically, a different instrument is required for the various diagnostic procedures. For example, the biopsy needle assemblies for prostate biopsies are much larger than those used for breast biopsies. In both instances, however, the same operating instrument or mechanism may be employed to attain movement of the cannula and stylet needles of the assembly. As such, it is desirable to support the needle assembly properly during the biopsy procedure, and avoid undesired movement of the needles which may have been previously positioned using sophisticated imaging equipment. The problem of supporting biopsy needles of differing sizes is eliminated with an instrument constructed in accordance with the present invention.

SUMMARY OF THE INVENTION

In accordance with the present invention, a tissue sampling instrument for use with various needle gauges to extract tissue samples includes an adjustable support structure including a plurality of needle support seats having different seat dimensions corresponding to respective different needle circumferences. The seats are arranged on the support structure to enable selective access and positioning of each seat in order to selectively support the corresponding needle circumference thereon and ensure accurate linear longitudinal motion of the needle against the selected seat in the tissue sampling procedure. The support structure can be rotatably mounted on an end wall of the body of the instrument so that the supported needle projects from the end wall, in a preferred illustrated embodiment of the invention.

In a preferred embodiment of the instrument, the position of the selected seat forms an interruption in an upper edge of the end wall to enable vertical insertion and removal of the selected needle with respect to the seat and the end wall. The end wall provides detented journalling for rotation of the support structure to provide indexing the selective rotational positioning of a seat.

BRIEF DESCRIPTION OF THE DRAWINGS

FIG. 3 is a fragmentary, exploded perspective view of one end of the instrument housing in FIGS. 1 and 2, illustrating a rotatable needle support structure;

FIG. 4 is an exterior plan view of the rotatable support structure shown in FIG. 3;

FIG. 5 is a sectional view taken along a plane indicated by line 5—5 in FIG. 1; and FIG. 6 is a sectional view along a plane indicated by line 6—6 in FIG. 5.

DESCRIPTION OF THE ILLUSTRATED EMBODIMENT

Figure 1:
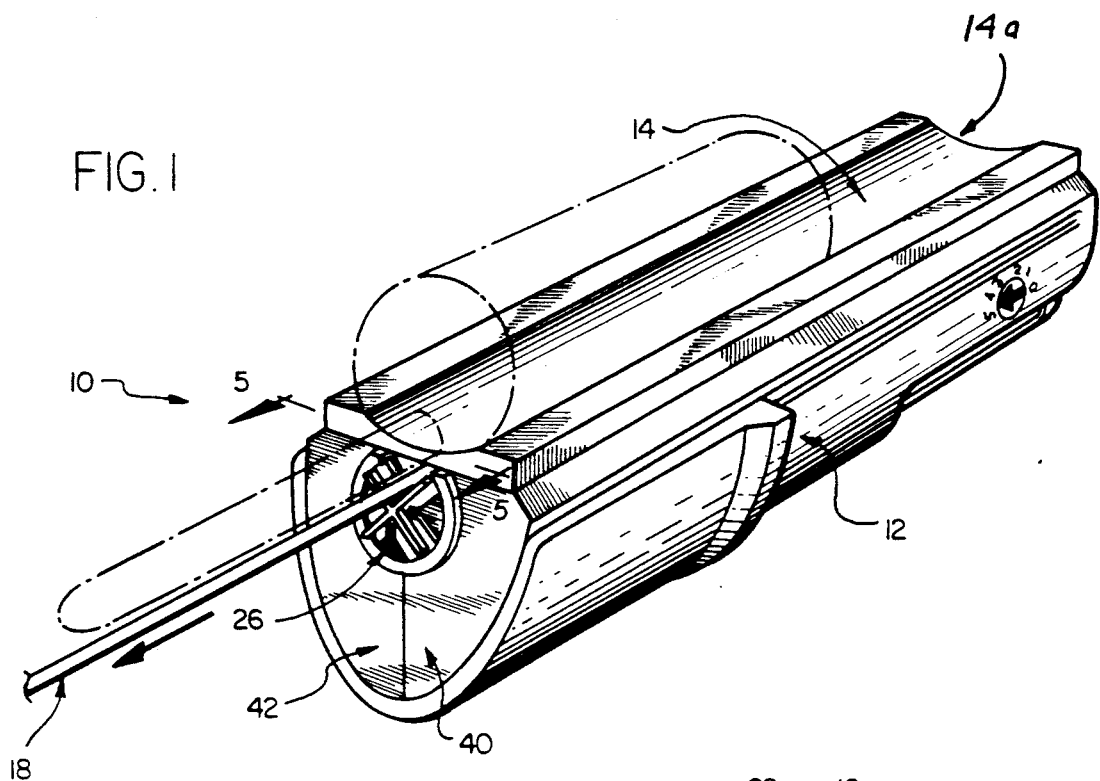
FIG. 1 is a perspective view of one embodiment of the tissue sampling in accordance with the present invention.
Figure 2:
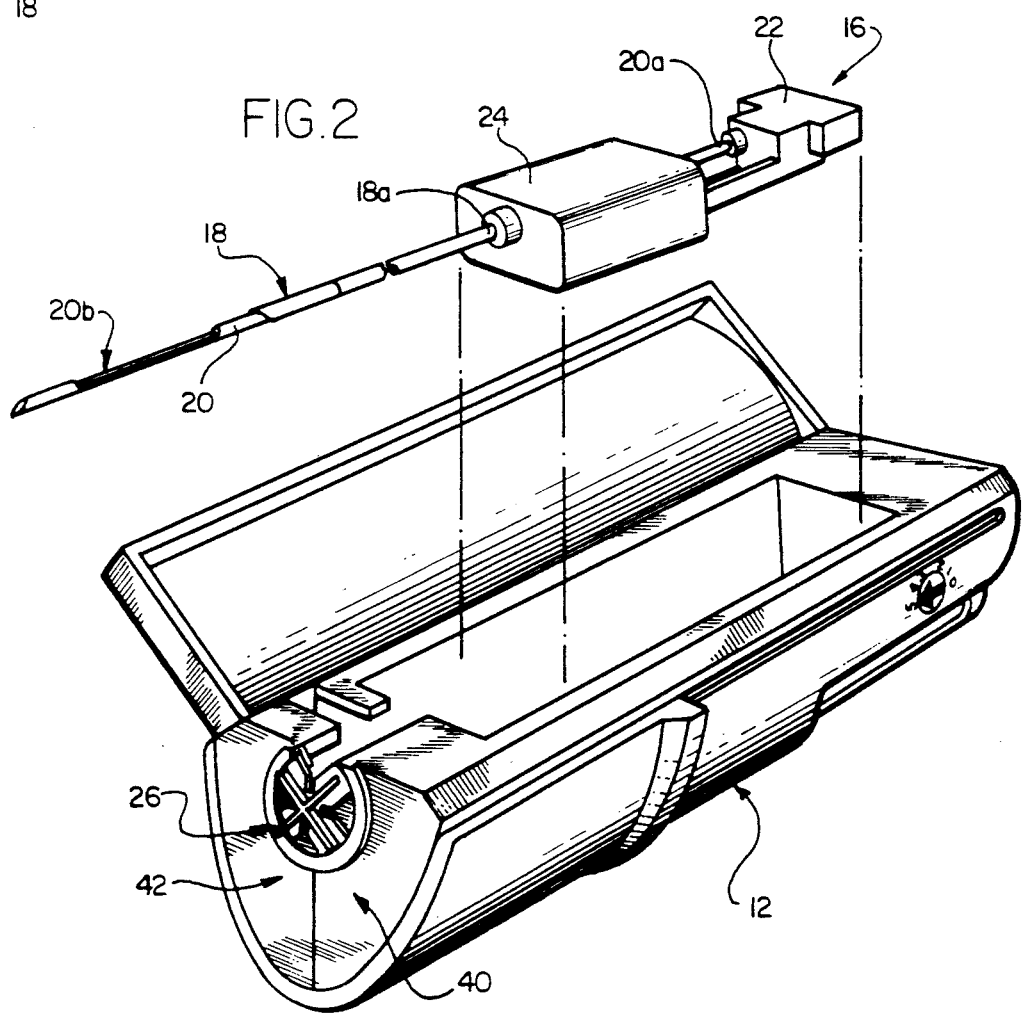
FIG. 2 is a perspective view of the instrument in FIG. 1 and illustrating a needle assembly removed from the housing of the instrument.

Referring to FIGS. 1 and 2, one embodiment of a tissue sampling instrument or actuator in accordance with the present invention is designated generally by reference character 10. The instrument 10 includes a housing 12 which has a hinged cover 14 that opens to enable installation and removal of a needle assembly generally designated by reference character 16. The cover 14 has a shallow channel 14a to accommodate an ultrasound probing instrument, shown in dotted outline, for aiding in location of the tissue to be sampled. The probe portion of the instrument will be disposed closely adjacent the needle assembly 16 due to the groove 14a.

The needle assembly 16 includes an outer cannula 18 through which a stylet 20 extends and cooperates to cut and capture a core of the diagnostic tissue. The rear end 20a of the stylet 20 is secured within a stylet hub or carriage 22 and the rear end 18a of the cannula 18 is secured within a cannula hub or carriage 24. The carriages 22 and 24 are coupled to enable limited relative sliding and displacement of the carriages, and the carriages can be uncoupled to allow the stylet 20 to be entirely withdrawn from the cannula 18 in order to enable the tissue core sample to be removed from the notch 20b in the stylet 20, and also to permit a syringe to be attached to the cannula carriage for obtaining a body fluid sample.

Referring again to FIG. 2, the needle assembly 16 is vertically lowered or disposed into the opened housing 12 so that the cannula 18 is laid into and projects from a rotatable support dial 26 mounted in the front wall 40,42 of the housing 12. Within the housing 12 a carriage drive mechanism (not shown) actuates one or more needle motions for example as described in the aforementioned U.S. Pat. No. 5,121,751. Conventional, variously sized cannulas 18 ranging in diameter from 0.032 inch (21 GA) to 0.083 inch (14 GA) can be selectively supported by the rotatable support dial 26 which has a series of distinct needle support seats 28 on the dial 26 with the corresponding gauge designations 30 labeled thereon with the digits straddle the respective seat 28 as best shown in FIGS. 3 and 4. The seats 28 are formed as radially inner, arcuate extensions of guide indentations 32 sequentially formed in the periphery of a main wheel portion 34 of the dial 26. Thus, irrespective of the size of biopsy needle being used, the needle will be supported and held by the support dial 26. This tends to avoid any premature movement of the needle which could result in misalignment.

Referring again to FIGS. 1-3, the instrument housing 12 has generally vertically split housing halves 36 and 38 each having a respective integrally formed end wall portion 40,42. Each of the end wall portions 40 and 42 includes a respective interior edge recess 44,46 which cooperate to journal a bearing hub portion 48 of the dial 26. When the end wall portions 40 and 42 are joined in assembly of the housing halves 36 and 38 as shown in FIGS. 1 and 2, the wheel portion 34 of the dial 26 is peripherally confined by respective channel-shaped, arcuate flanges 50 and 52 which extend from the outer surface of the end wall portions 40 and 42, respectively, as best shown in FIG. 3. A cruciform-shaped gripping portion 54 extends outwardly from the surface of the dial wheel 34 for manual rotation of the dial 26 in order to position the support seat 28 of the proper gauge corresponding to the selected cannula diameter 18 in the tissue sampling operation of the instrument, for example as more fully described in the aforementioned U.S. Pat. No. 5,121,751.

In order to provide convenient and stabilized indexing in the selective rotation of the dial 26, the end wall journalling recesses 44 and 46 include a series of flats 56 which engage mating flats 58 on the dial hub 48. The recess flats 56 yield slightly to the rotation of the hub flats 58 to provide detented rotation of the dial 26 and hub 48 as successive hub flats 58 engage the recess flats 56 and create detented indexing to stabilize the selected seat 28 in the loading position which supports the correspondingly gauged cannula 18 as shown in FIG. 5, and maintain stationary support of the cannula during its longitudinal motion against the seat in the tissue sampling operation.

While a particular embodiment of the tissue sampling instrument have been described herein, it will be obvious to those skilled in the art that changes and modifications in various aspects may be made without departing from the broad scope of the invention. Consequently, the scope of the invention is not limited by any particular embodiment but is defined by the appended claims and the equivalents thereof.

I claim:

1. A tissue sampling instrument for use with various needle gauges to extract a tissue sample, said instrument comprising: a support structure including a plurality of needle-support seats having different seat dimensions corresponding to respective different needle circumferences, said seats being arranged on said support structure to enable selective access and positioning of each said seat in order to selectively support said corresponding needle circumference thereon for tissue extraction operation wherein said instrument comprises a generally elongate body and said support structure is secured on an end wall of said body, said seats being arranged to enable perpendicular projection of the selected needle from said end wall, and wherein said selective positioning of said seat forms an interruption in an upper edge of said end wall to enable vertical and transverse insertion and removal of said selected needle with respect to said seat and end wall.

2. The instrument according to claim 1 wherein said plurality of seats are arranged in a series of respective peripheral notches on the said support structure.

3. The instrument according to claim 2 wherein each said notch forms an inner portion of a respective guide indentation from a peripheral edge of said support structure such that said guide indentation provides guidance for insertion of said selected needle into said respective seat.

4. The instrument according to claim 1 wherein said plurality of seats are arcuately arranged on said support structure which is journalled on said instrument to enable rotational selection of said seat positioning.

5. The instrument according to claim 4 further comprising an elongate body and said support structure is journalled on an end wall of said body.

6. The instrument according to claim 4 wherein said detent means comprises a series of flat surfaces formed in said journal structure against which a plurality of corresponding flats on a hub of said support structure are successively engaged in frictional rotation to provide said indexing.

7. The instrument according to claim 1 wherein said end wall includes a journal structure supporting rotation of said support structure and said journal structure includes detent means for indexing said selective rotational positioning of each said seat.

* * * * *